United States Patent [19]
Vic et al.

[11] Patent Number: 5,817,904
[45] Date of Patent: Oct. 6, 1998

[54] METHOD FOR THE CONVERSION OF METHANE INTO LONGER CHAIN HYDROCARBONS

[75] Inventors: Sebastian Vic; Miguel A. Peña; Pilar Terreros; Juan P. Gomez; José L. Garcia-Fierro; Juan M. Jimenez, all of Madrid, Spain

[73] Assignee: Repsol Petroleo S.A., Madrid, Spain

[21] Appl. No.: 479,002

[22] Filed: Jun. 7, 1995

Related U.S. Application Data

[63] Continuation of Ser. No. 989,131, Dec. 11, 1992, abandoned.

[51] Int. Cl.$^6$ ..................................................... C07C 2/00
[52] U.S. Cl. ........................ 585/500; 585/415; 585/417; 585/418; 585/654; 585/656; 585/658; 585/943
[58] Field of Search .................................. 585/500, 415, 585/417, 418, 654, 656, 658, 943

[56] References Cited

U.S. PATENT DOCUMENTS

| | | | |
|---|---|---|---|
| 4,495,374 | 1/1985 | Jones et al. | 585/943 |
| 4,499,322 | 2/1985 | Jones et al. | 585/943 |
| 4,523,049 | 6/1985 | Jones et al. | 585/500 |
| 4,547,611 | 10/1985 | Jones et al. | 585/500 |
| 4,650,781 | 3/1987 | Jones et al. | 585/500 |
| 4,654,459 | 3/1987 | Sofranko et al. | 585/500 |
| 4,777,313 | 10/1988 | Sofranko et al. | 585/500 |
| 4,939,310 | 7/1990 | Wade | 585/500 |
| 4,981,829 | 1/1991 | Shutt et al. | 585/500 |
| 5,160,502 | 11/1992 | Kimble et al. | 585/500 |

*Primary Examiner*—Elizabeth D. Wood
*Attorney, Agent, or Firm*—Cushman, Darby & Cushman IP Group of Pillsbury, Madison & Sutro

[57] ABSTRACT

A method for converting methane by an oxidative coupling reaction to longer chain hydrocarbons comprising cofeeding methane and oxygen simultaneously and continuously into a reaction zone to form a mixture, contacting said methane and oxygen mixture under oxidative coupling reaction conditions with a solid catalyst consisting essentially of manganese oxide and silicon oxide, promoted with an alkaline metal and non metal, to form longer chain hydrocarbons wherein the manganese, silicon oxide, alkali metal and non metal are present in a molar ratio 0–0.5:93.2–93.7:4.2:2.1.

5 Claims, 1 Drawing Sheet

METHOD FOR THE CONVERSION OF METHANE INTO LONGER CHAIN HYDROCARBONS

This is a continuation of application Ser. No. 07/989,131, filed on Dec. 11, 1992, which was abandoned upon the filing hereof.

The invention relates to a catalytic method useful in the conversion of methane into higher hydrocarbons, particularly ethylene and ethane, via an oxidative coupling reaction of methane (OCM). The invention also refers to an improved catalyst composition for carrying out said method.

BACKGROUND OF THE INVENTION AND DESCRIPTION OF THE PRIOR ART

Natural gas, whose major component is methane, represents today the largest energy source. Its reserves are much larger than that of other fossil fuels, but are usually located in remote areas far enough from the market spots. Moreover, the methane molecule presents unfavourable critical constants which make it very difficult to be liquefied. Accordingly, the conversion of methane into easier liquefiable hydrocarbons, i.e. $C_2+$ hydrocarbons, becomes imperative.

The discovery by Keller and Bhasin (J. Catal. 73,9,1982) that methane can be dimerised over redox type oxides was an improvement in this field. The disclosure of this work mentioned that methane can readily be converted over appropriate catalysts into $C_2+$ hydrocarbons with a low yield and ranges of methane conversion between 9–48%. Detailed analysis of the results of the oxidative coupling led to the conclusion that this reaction is only selective for $C_2+$ hydrocarbons when no oxygen is present in the gas phase, that is, the coupling is achieved by the lattice oxygen of the catalyst agent. Since lattice oxygen available from a redox system is limited for given reaction conditions, the reaction progress will also be limited. Furthermore, the cyclic operation implies large investment and significant time wasted for operation.

U.S. Pat. No. 4,443,644 discloses a process for the conversion of methane into higher hydrocarbons by contacting a methane-containing gas and solid particles comprising a reducible oxide of antimony at a temperature ranging from 500°–1000° C. to form higher hydrocarbon products, byproduct water and particles comprising a reduced oxide of antimony. The particles comprising a reduced oxide of antimony are removed and regenerated by contact with an oxygen-containing gas at a temperature ranging from 300°–1200° C. to form particles comprising a reducible oxide of antimony, which can be used anew. Parallel methods with different metal oxides are described in U.S. Pat. Nos. 4,443,645 (oxide of germanium); 4,443,646 (oxide of bismuth); 4,443,647 (oxide of lead); 4,443,648 (oxide of indium) and 4,443,649 (oxide of manganese) . However, the yields for $C_2+$ hydrocarbons (as quoted in the examples) are low, reaching a top of 2.1% with a manganese catalyst.

Catalysts comprising supported-Mn using different promoting materials provide an improvement in both selectivity and yield to $C_2+$ hydrocarbons when the above-mentioned cyclic operation is employed (U.S. Pat. Nos. 4,495,374; 4,499,322; 4,547,611; 4,650,781; 4,654,459; 4,777,313, and 4,939,310).

If a solid with an analogous composition is implemented in a co-fed operation, the performance of the process decreases substantially (U.S. Pat. Nos. 4,523,049 and 4,981,829).

Further improvement was proposed by U.S. Pat. No. 4,608,449 when disclosing oxidative coupling of methane by co-feeding methane and oxygen in a reactor at temperatures of 500°–900° C., with molar ratios $CH_4/O_2$ higher than 2 and an overall pressure higher than 1 bar. It is also disclosed that propane is the higher hydrocarbon among $C_2+$ with an overall selectivity to $C_2+$ hydrocarbons (ethane, ethylene and propane) no higher than 65%, and that unreacted methane can be recirculated into the reactor. The catalysts used are metal oxides of B elements of Periodic Table, including lead, bismuth, indium, cadmium, antimony, tin and thalium, either massive or supported on alumina, silica, titania and silicon carbide, which operate in temperature ranges of 500°–900° C. Under these rather severe conditions a part of the metal (i.e. tin) oxide is lost by vaporization, particularly for long periods on-stream. To overcome this inconvenience, U.S. Pat. No. 4,780,449 discloses much more stable catalytic systems for OCM reaction including alkaline-earth and lanthanides, which can be used either alone or with promoters such as alkaline, alkaline-earth and lanthanide oxides up to 50% by weight.

Also, incorporation of halogens to the catalysts (U.S. Pat. No. 4,914,252) or feeding with halogenated hydrocarbons has been described. Halocompounds have the property of generating halogen radicals at high temperatures, which then act as initiators of methyl radicals from methane molecules. Whichever the method, halogen is consumed during OCM reaction with the subsequent production of the corresponding haloacid, which implies serious corrosion problems and requires careful control of the analytical system.

Therefore, it might be concluded that there is no general principle to predict the catalytic behaviour of a given system. Researchers on the art often refer to physical phenomena, such as adsorption-desorption of oxygen species from the catalyst surface or mass, or generation of free radicals, etc. Consequently, the solid materials used in the processes are usually called activators, promoters or catalysts. In this description, the term catalyst will be employed.

Finally, as the dimerization reaction is extremely complex, the adequacy of a given catalyst is unpredictable. It must be also kept in mind that both methane conversion and selectivity to a given product depend on the reaction conditions and mode of operating the reaction, and there is little basis for predicting what operation conditions will result in high conversion yields to a given product, i.e. ethylene and ethane.

SUMMARY OF THE INVENTION

It is an object of the invention to provide an improved method for the conversion of methane into longer chain hydrocarbons, with a high selectivity, particularly to ethylene and ethane.

Another object is to provide an OCM method which can be carried out with low cost starting materials and under rather moderate reaction conditions.

It is also an object of the present invention to provide an improved catalyst composition for carrying out the OCM reaction.

According to the invention, methane can be converted into longer chain hydrocarbons, particularly ethylene and ethane, by following a method wherein a methane and oxygen mixture is contacted with a solid catalyst comprising manganese, silicon or aluminum, and alkaline element and a non-metallic element.

The reaction is carried out at atmospheric pressure in a fixed bed flow reactor which operates under the appropriate conditions leading to OCM reaction. The alkaline element is preferably potassium, and the non-metallic element is preferably phosphorus.

Also preferably, the catalyst comprises manganese, silicon, potassium and phosphorus in a molar ratio 0–0.5:93.2–93.7:4.2:2.1, respectively.

The method of the invention is also distinguished from known processes in that the reactant mixture is fed into a fixed bed reactor without diluent; the reaction temperature is kept within a relatively low range of temperature, 600°–850° C.; the catalyst is prepared by combining the precursor materials, calcining in air atmosphere, and preheating within the reactor in the reactant gas mixture before starting catalytic action; manganese and the alkaline element are incorporated simultaneously to the catalyst, and aluminum or silicon are incorporated as oxides during the preparation of the catalyst. All these features lead to large $C_2+$ yields and lower cost of operation.

DRAWING

FIGS. 1 and 2 are ternary diagrams showing the composition of examples of catalysts according to the invention.

DETAILED DESCRIPTION OF THE INVENTION

The gas fed is methane, although a mixture with non interfering gases can be used if the methane content is within 25–100% molar. Other alternatives to natural gas, as synthetic natural gas (SNG) and products resulting from gasification of carbide materials or from anaerobic digestion of biomass can be also used. The presence of minor amounts of longer chain hydrocarbons in the above feeds does not require further purifications.

The preferred catalysts of the invention for the OCM reaction are mixtures of manganese oxide-silicon oxide or manganese oxide-aluminum oxide, promoted with variable amounts of alkaline metals, preferable potassium, and non-metals, preferably phosphorus.

The amounts of manganese range from 0–8% molar, preferably between 0–1% molar. The alkaline element, potassium, ranges from 0–40% molar, preferably 3–6% molar. The phosphorus content ranges from 0–15% molar, preferably 1.5–3% molar. The balance up to 100% molar is silicon or aluminum.

Figure 1:
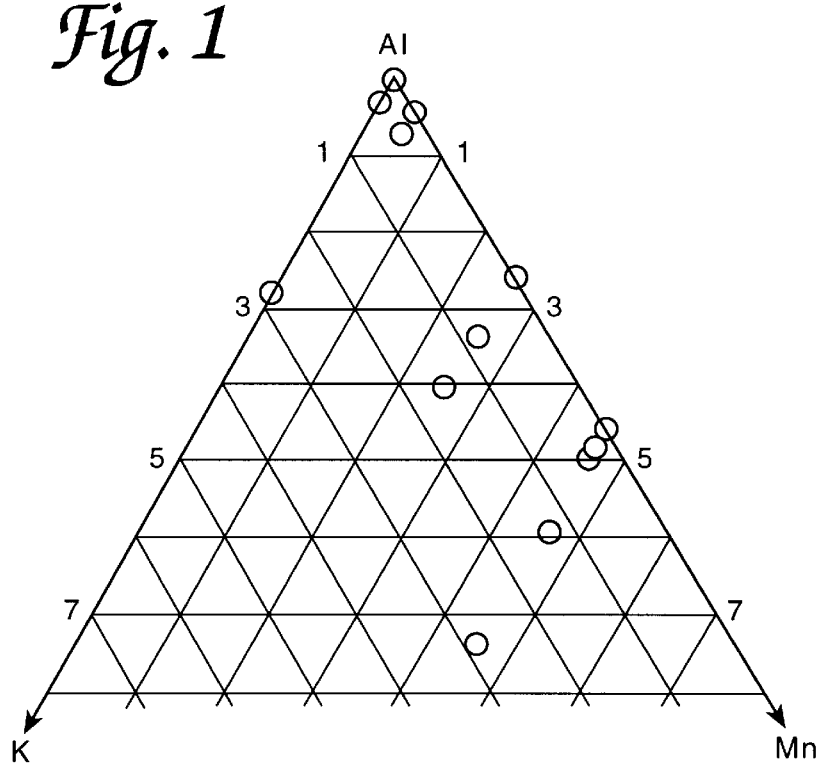
Figure 2:
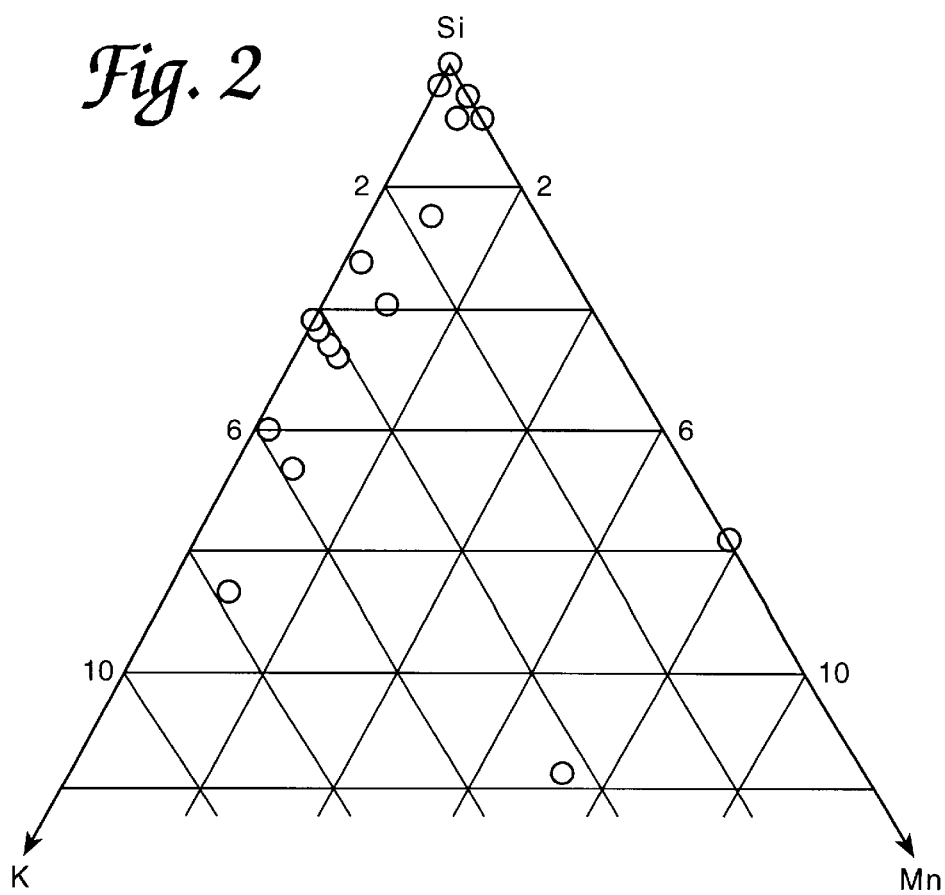

The composition of the different catalysts is expressed as the molar percentage of manganese, potassium and silicon or aluminum, as represented in the ternary diagrams of FIGS. 1 and 2. It should be noted that only the manganese-potassium-silicon series contains phosphorus, and that the molar ratio phosphorus/potassium was 1:2. For simplicity, two highly loaded potassium catalyst preparations (approx. 36% molar) have not been included in this latter series.

The preferred catalyst results from the combination Mn—Si—K—P, with a molar ratio of 0–0.5:93.2–93.7:4.2:2.1, respectively. The catalyst can be prepared by complete solubilization of alkaline (potassium), phosphorus and manganese precursors. After that, the solubilized materials are contacted with the corresponding silicon or aluminum compound. The resulting mixture is firstly pre-heated to remove volatile elements and then heated at temperatures ranging from 600°–1000° C., preferably 700°–850° C. Moreover, physical shape of the catalyst can accordingly be selected with conventional techniques of the art, namely tablets, beads or extrudates. These operations are carried out in an independent synthesis system.

In accordance with the most extended procedure for the oxidative coupling of methane to higher hydrocarbons, particularly ethylene and ethane, the reaction is carried out in a fixed bed flow reactor by co-feeding both methane and oxygen. This mode of operation provides a great flexibility for the control of the operation parameters and of the overall process, and simultaneously reduces the extremely long time of operation required by the cyclic feeding. The temperature required for the oxidative coupling is in the range of 500°–1000° C., although a narrower range of 600°–800° C. is preferred. The reactor operates in all cases at pressures about 1 bar, and only a slight increase is introduced as a consequence of the pressure drop through the catalyst bed and other flow elements of the system. This feature simplifies to a great extent the control of the operation since a very simple feed system and reactor control are required. Another important advantage arising from these conditions is that of reducing the probability of an explosion. The residence times of reactants are in the range of 0.5–50 g.h/mol, the range of 1–30 g.h/mol being preferable.

According to the invention it has been found that an enhanced methane conversion into longer chain hydrocarbons, particularly ethylene and ethane, via OCM reaction, can be achieved by contacting a methane and oxygen mixture on a catalyst comprising manganese, silicon or aluminum, an alkaline element, preferably potassium, and phosphorus, with a preferred Mn/Si(Al)/K/P molar ratio of 0–0.5:93.2–93.7:4.2:2.1, respectively, under reaction conditions leading to an effective oxidative coupling of methane.

The following examples are given to illustrate specific embodiments of the method according to the invention.

The composition of several catalyst samples, expressed as molar percentage of the constituent elements, is shown in Table I. There are two groups of preparations with the same composition, 1 and 2, 5 and 6. Among these, small differences exist with respect to the general preparation procedure described above. While the pH of the solubilization medium of manganese, potassium and phosphorus precursors was adjusted to the acid region for preparations of catalysts 1 and 5, it remained uncontrolled for all the other catalysts.

TABLE I

| MOLAR COMPOSITION (%) OF THE CATALYSTS | | | | | |
| --- | --- | --- | --- | --- | --- |
| CATALYST | Mn | Si | Al | K | P |
| 1 | 0.0 | 93.7 | 0.0 | 4.2 | 2.1 |
| 2 | 0.0 | 93.7 | 0.0 | 4.2 | 2.1 |
| 3 | 0.2 | 93.5 | 0.0 | 4.2 | 2.1 |
| 4 | 0.2 | 95.3 | 0.0 | 3.0 | 1.5 |
| 5 | 0.5 | 93.2 | 0.0 | 4.2 | 2.1 |
| 6 | 0.5 | 93.2 | 0.0 | 4.2 | 2.1 |
| 7 | 0.8 | 90.5 | 0.0 | 5.8 | 2.9 |
| 8 | 0.9 | 99.1 | 0.0 | 0.0 | 0.0 |
| 9 | 2.6 | 0.0 | 95.9 | 1.5 | 0.0 |

The data of Table II provides a summary of both reaction conditions and catalyst performance for each sample. It should be noted that two reaction conditions, W/F=20 g.h/mol for a molar ratio $CH_4/O_2=4$ and W/F=10 g.h/mol for a molar ratio $CH_4/O_2=5$, were used. For comparative purposes among the two groups, data of catalyst 5 under the two reaction conditions, 5 and 5a, are shown.

TABLE II

| Catalyst sample | 1 | 1 | 1 | 2 | 2 | 2 |
|---|---|---|---|---|---|---|
| Residence time (g.h/mol) | 20 | 20 | 20 | 20 | 20 | 20 |
| Molar ratio CH$_4$/O$_2$ | 4 | 4 | 4 | 4 | 4 | 4 |
| Pressure (bar) | 1 | 1 | 1 | 1 | 1 | 1 |
| Temperature (°C.) | 700 | 750 | 800 | 700 | 750 | 800 |
| Methane conversion % | 14.0 | 23.4 | 25.9 | 11.9 | 20.8 | 24.2 |
| Selectivity to C$_2$+ % | 15.5 | 39.9 | 51.0 | 7.3 | 32.1 | 47.5 |
| Ethylene yield % | 0.80 | 5.05 | 8.16 | 0.26 | 3.38 | 7.00 |
| Ethane yield % | 1.32 | 3.62 | 3.67 | 0.59 | 2.90 | 3.47 |
| CO yield % | 8.54 | 6.92 | 4.42 | 8.47 | 6.85 | 4.10 |
| CO$_2$ yield % | 3.29 | 7.15 | 8.25 | 2.59 | 7.29 | 8.63 |

| Catalyst sample | 3 | 3 | 3 | 4 | 4 | 4 |
|---|---|---|---|---|---|---|
| Residence time (g.h/mol) | 20 | 20 | 20 | 20 | 20 | 20 |
| Molar ratio CH$_{4/O2}$ | 4 | 4 | 4 | 4 | 4 | 4 |
| Pressure (bar) | 1 | 1 | 1 | 1 | 1 | 1 |
| Temperature (°C.) | 700 | 750 | 800 | 700 | 750 | 800 |
| Methane conversion % | 16.2 | 18.6 | 22.1 | 17.0 | 19.6 | 22.2 |
| Selectivity to C$_2$+ % | 8.3 | 22.2 | 37.9 | 10.8 | 26.3 | 37.8 |
| Ethylene yield % | 0.33 | 1.68 | 4.64 | 0.52 | 2.32 | 4.83 |
| Ethane yield % | 0.98 | 2.31 | 3.05 | 1.27 | 2.63 | 2.93 |
| CO yield % | 5.25 | 4.92 | 3.84 | 6.12 | 4.95 | 3.91 |
| CO$_2$ yield % | 9.59 | 9.53 | 9.88 | 9.05 | 9.51 | 9.89 |

| Catalyst sample | 5 | 5 | 5 | 5a | 5a | 5a |
|---|---|---|---|---|---|---|
| Residence time (g.h/mol) | 20 | 20 | 20 | 10 | 10 | 10 |
| Molar ratio CH$_4$/O$_2$ | 4 | 4 | 4 | 5 | 5 | 5 |
| Pressure (bar) | 1 | 1 | 1 | 1 | 1 | 1 |
| Temperature (°C.) | 700 | 750 | 800 | 700 | 750 | 800 |
| Methane conversion % | 9.9 | 21.7 | 25.5 | 12.5 | 17.8 | 18.5 |
| Selectivity to C$_2$+ % | 17.5 | 37.9 | 50.0 | 23.1 | 31.3 | 21.2 |
| Ethylene yield % | 0.53 | 4.30 | 8.00 | 1.28 | 3.70 | 3.45 |
| Ethane yield % | 1.16 | 3.28 | 3.17 | 1.60 | 1.87 | 0.47 |
| CO yield % | 5.14 | 8.03 | 7.55 | — | — | — |
| CO$_2$ yield % | 3.03 | 5.47 | 5.20 | — | — | — |

| Catalyst sample | 6 | 6 | 6 | 7 | 7 | 7 |
|---|---|---|---|---|---|---|
| Residence time (g.h/mol) | 20 | 20 | 20 | 10 | 10 | 10 |
| Molar ratio CH$_4$/O$_2$ | 4 | 4 | 4 | 5 | 5 | 5 |
| Pressure (bar) | 1 | 1 | 1 | 1 | 1 | 1 |
| Temperature (°C.) | 700 | 750 | 800 | 700 | 750 | 800 |
| Methane conversion % | 16.6 | 18.5 | 22.2 | 13.8 | 16.9 | — |
| Selectivity to C$_2$+ % | 7.1 | 21.0 | 37.6 | 10.1 | 25.5 | — |
| Ethylene yield % | 0.31 | 1.57 | 4.62 | — | — | — |
| Ethane yield % | 0.86 | 2.18 | 3.07 | — | — | — |
| CO yield % | 5.20 | 4.23 | 3.40 | — | — | — |
| CO$_2$ yield % | 10.22 | 10.4 | 10.45 | — | — | — |

| Catalyst sample | 8 | 8 | 8 | 9 | 9 | 9 |
|---|---|---|---|---|---|---|
| Residence time (q.h/mol) | 10 | 10 | 10 | 10 | 10 | 10 |
| Molar ratio CH$_4$/O$_2$ | 5 | 5 | 5 | 5 | 5 | 5 |
| Pressure (bar) | 1 | 1 | 1 | 1 | 1 | 1 |
| Temperature (°C.) | 700 | 750 | 800 | 700 | 750 | 800 |
| Methane conversion % | 14.9 | 14.6 | — | 12.6 | 14.5 | 18.3 |
| Selectivity to C$_2$+ % | 4.7 | 17.6 | — | 9.8 | 22.9 | 21.6 |
| Ethylene yield % | — | — | — | 0.40 | 2.20 | 3.44 |
| Ethane yield % | — | — | — | 0.83 | 1.13 | 0.51 |
| CO yield % | — | — | — | — | — | — |
| CO$_2$ yield % | — | — | — | — | — | — |

We claim:

1. A method for converting methane by an oxidative coupling reaction to longer chain hydrocarbons comprising cofeeding methane and oxygen simultaneously and continuously, having a methane/oxygen ratio of about 4, into a reaction zone to form a mixture, contacting said methane and oxygen mixture under oxidative coupling reaction conditions with a solid catalyst consisting essentially of manganese oxide and silicon oxide, promoted with potassium and phosphorus, to form longer chain hydrocarbons wherein the manganese, silicon oxide, potassium and phosphorus are present in a molar ratio 0–0.5:93.2–93.7:4.2:2.1.

2. A method according to claim 1, wherein said methane and oxygen mixture is fed into a fixed bed reactor without diluent.

3. A method, according to claim 1, wherein reaction temperature is kept within the range 600°–850° C.

4. A method according to claim 1 wherein the longer chain hydrocarbons formed are ethylene and ethane, in yields in the range 4.0–8.2% for ethylene and in yields in the range 3.0–3.7% for ethane, based on total fed methane.

5. A method according to claim 1 wherein the oxidative coupling reaction conditions include a pressure of operation of 1 bar and the residence time is in the range 10 to 20 gh/mol.

* * * * *